United States Patent
Nobles et al.

(10) Patent No.: US 11,400,273 B2
(45) Date of Patent: Aug. 2, 2022

(54) CONSTRICTION VALVE

(71) Applicant: HeartStitch, Inc., Fountain Valley, CA (US)

(72) Inventors: Anthony Nobles, Fountain Valley, CA (US); Christian Willer, Zwickau (DE)

(73) Assignee: HEARTSTITCH, INC., Fountain Valley, CA (US)

(*) Notice: Subject to any disclaimer, the term of this patent is extended or adjusted under 35 U.S.C. 154(b) by 0 days.

(21) Appl. No.: 16/234,431

(22) Filed: Dec. 27, 2018

(65) Prior Publication Data

US 2019/0126026 A1    May 2, 2019

Related U.S. Application Data

(62) Division of application No. 15/131,714, filed on Apr. 18, 2016, now Pat. No. 10,183,159.

(Continued)

(51) Int. Cl.
*A61M 39/22* (2006.01)
*F16K 31/44* (2006.01)
(Continued)

(52) U.S. Cl.
CPC ............ *A61M 39/22* (2013.01); *F16K 7/08* (2013.01); *F16K 31/445* (2013.01); *A61M 39/26* (2013.01);
(Continued)

(58) Field of Classification Search
CPC ............ A61M 39/22; A61M 39/288; A61M 2039/226; A61M 39/26; A61M 25/0071;
(Continued)

(56) References Cited

U.S. PATENT DOCUMENTS 3,383,131 A    5/1968  Rosfelder
4,094,492 A    6/1978  Beeman et al.
(Continued)

FOREIGN PATENT DOCUMENTS

WO    1993003777    3/1993
WO    2004112880    12/2004
(Continued)

OTHER PUBLICATIONS

"Edwards Gains FDA Approval for Next Generation Sapien XT Heart Valve System", Medical Hoizons, an MRC Media Group Company, http://www.meical-horizons.net/blog-view.php?id=499, Jun. 17, 2014.

(Continued)

*Primary Examiner* — Nilay J Shah
(74) *Attorney, Agent, or Firm* — Fish IP Law, LLP

(57) ABSTRACT

Constriction valves for catheters and method of using constriction valves are presented. The catheter valve has a conduit comprising mesh defining a lumen. The catheter also has a biasing member that is configured to bias the lumen from an open position to a closed position by altering an effective length of the conduit or altering the circumference of the conduit. The biasing member is further configured to change its configuration by changes of intraluminal pressure of the valve. A user can insert a tool into a catheter having a valve by manipulating the valve to expand a substantially closed lumen by compressing the biasing member, twisting the biasing member, or pulling on a cord coupled with the valve.

13 Claims, 9 Drawing Sheets

Related U.S. Application Data

(60) Provisional application No. 62/267,777, filed on Dec. 15, 2015.

(51) Int. Cl.
*F16K 7/08* (2006.01)
*A61M 39/26* (2006.01)
*F16K 7/06* (2006.01)
*F16K 7/04* (2006.01)
*A61M 39/28* (2006.01)
*F16K 21/04* (2006.01)

(52) U.S. Cl.
CPC ..... *A61M 39/288* (2013.01); *A61M 2039/226* (2013.01); *F16K 7/04* (2013.01); *F16K 7/06* (2013.01); *F16K 21/04* (2013.01)

(58) Field of Classification Search
CPC ............ A61M 2025/085; F16K 31/445; F16K 21/00; F16K 21/04; F16K 7/08; F16K 7/02; F16K 7/04; F16K 7/06
See application file for complete search history.

(56) References Cited

U.S. PATENT DOCUMENTS

| | | | |
|---|---|---|---|
| 4,540,411 A | 9/1985 | Bodicky | |
| 4,570,898 A * | 2/1986 | Staeubli | A61M 39/288 251/321 |
| 5,112,324 A | 5/1992 | Wallace | |
| 5,179,934 A * | 1/1993 | Nagayoshi | A61B 1/00183 600/152 |
| 5,197,955 A | 3/1993 | Stephens et al. | |
| 5,211,370 A * | 5/1993 | Powers | A61B 17/3462 251/212 |
| 5,582,165 A | 12/1996 | Bryan et al. | |
| 5,814,026 A | 9/1998 | Yoon | |
| 6,270,053 B1 | 8/2001 | Eshel | |
| 6,450,989 B2 | 9/2002 | Dubrul et al. | |
| 6,475,135 B1 | 11/2002 | Levy | |
| 7,914,492 B2 | 3/2011 | Heuser | |
| 7,981,086 B2 * | 7/2011 | Focht | A61B 17/3498 604/164.01 |
| 8,079,973 B2 | 12/2011 | Herrig et al. | |
| 8,132,783 B2 | 3/2012 | Luebbers | |
| 8,900,168 B2 | 12/2014 | Yamashiro et al. | |
| 2004/0015177 A1 | 1/2004 | Chu | |
| 2005/0038396 A1 * | 2/2005 | Claude | A61M 1/3655 604/246 |
| 2005/0059934 A1 * | 3/2005 | Wenchell | A61B 17/3439 604/167.01 |
| 2005/0092944 A1 * | 5/2005 | Patterson | F16K 7/08 251/4 |
| 2005/0131344 A1 | 6/2005 | Godaire | |
| 2005/0209518 A1 * | 9/2005 | Sage | A61B 5/14532 600/366 |
| 2007/0118021 A1 | 5/2007 | Pokorney | |
| 2007/0161956 A1 | 7/2007 | Heuser | |
| 2011/0022063 A1 | 1/2011 | McClurg et al. | |
| 2014/0012235 A1 | 1/2014 | Pinchuk et al. | |
| 2014/0330309 A1 | 11/2014 | Gonzalez et al. | |

FOREIGN PATENT DOCUMENTS

| | | |
|---|---|---|
| WO | 2011094619 | 8/2011 |
| WO | 2015002832 | 1/2015 |
| WO | 2015031898 | 3/2015 |
| WO | 2015085145 | 6/2015 |

OTHER PUBLICATIONS

International Search Report and Written Opinion in corresponding International Application No. PCT/US2016/066850 dated Apr. 10, 2017, 19 pages.

* cited by examiner

CONSTRICTION VALVE

This application is a divisional application of U.S. Pat. No. 10,183,159, filed Apr. 18, 2018, which claims the benefit of and priority to U.S. Provisional Patent Application No. 62/267,777, filed Dec. 15, 2015, each of which are incorporated herein in their entirety by reference.

FIELD OF THE INVENTION

The field of the invention is a constriction valve for a catheter.

BACKGROUND

The background description includes information that may be useful in understanding the present invention. It is not an admission that any of the information provided herein is prior art or relevant to the presently claimed invention, or that any publication specifically or implicitly referenced is prior art.

Cardiac catheterization is a procedure to insert catheters into the heart via an artery or vein to diagnose or treat certain cardiovascular conditions. During cardiac catheterization, a catheter is inserted in an artery or vein in patient's neck, groin or arm. While a radial artery is often used as an access point to the heart during cardiac catheterization, a femoral artery is preferred because it has larger diameter, which allows the insertion of catheters in larger sizes. Once a catheter is properly inserted and positioned, various procedures can be performed by inserting devices into the lumen of the catheter. For example, coronary angiography can be performed by inserting a radio-dense tube to visualize the vasculature structures in the heart. In another example, balloon septostomy can be performed by inserting a balloon catheter to increase the blood flow in a septum of the heart.

Most common complications of cardiac catheterization include bleeding, thrombosis, and vascular trauma. These complications are especially problematic when the sheath of the catheter is relatively large (e.g., more than 8F), because arterial blood pressure at the site of the insertion is often more than 50 mmHg. Thus, blood spurting from the femoral artery can frequently occur when tubes are disoriented or dissociated from the catheter, or when a health provider replaces an inserted device. While manual compression has been most commonly used to reduce the complication, it requires a significant amount of pressure over the artery, which may cause pain for some patients, and deep vein thrombosis due to femoral artery compression and stasis.

Many technologies have been developed to prevent blood spurting without requiring manual compression over the patient's body. For example, U.S. Pat. No. 5,582,165 to Bryan discloses a catheter connector which is similar to Chinese finger trap. The catheter connector is configured to contract in diameter when the adaptor is pulled or stretched in an axial direction. This reduces blood spurting if the catheter is pulled or slipped out by inadvertent jerking of therapist or patient. U.S. Patent application No. 2004/0012235 to Pinchuk discloses a stretch-valve tube that applies a similar Chinese finger trap mechanism. In Pinchuk, when the flexible valve tube is stretched (e.g., when a urinary catheter is prematurely pulled out), the stretched portion collapses inwardly towards the longitudinal axis as the catheter body lengthens.

Others have sought to solve the problem by mechanically pressing in upon a portion of the catheter. For example, U.S. Pat. No. 7,914,492 to Heuser discloses a catheter introducer system where a portion of the catheter can be shut using a closing system similar to a camera shutter mechanism. In Heuser, a shutter positioned radially about a catheter shutter can be opened by inserting an opening device (e.g., a tip of needle) through the lumen of the catheter, shutter, and then closed automatically when the needle (or other opening device) is removed from the catheter.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved constriction valve systems for catheters.

SUMMARY OF THE INVENTION

The inventive subject matter provides systems, devices for a constriction valve for a catheter that can be used for cardiac catheterization, urinary catheterization or any other catheterization of the body area, especially those with high fluid pressures, and methods of using the constriction valve.

One aspect of the invention includes a catheter valve having a conduit which defines a lumen. The catheter valve can also include a spring that is configured to bias the lumen from an open position to a closed position by altering an effective length of the conduit by at least 1 mm.

Another aspect of the invention includes a catheter for insertion into a vascular structure. The catheter includes an elongated body, which has a proximal end and a distal end. The catheter further includes a valve positioned at the distal end of the elongated body. It is especially preferred that the valve includes a conduit defining a lumen, and a spring that is configured to bias the lumen from an open position to a closed position by altering an effective length of the conduit by at least 1 mm.

Another aspect of the invention includes a method of inserting a tool into a catheter, where the catheter has a valve with first and second finger contacts, and the method includes manipulating the valve to expand a substantially closed lumen. The step of manipulation can be achieved in any one or more of several different motions, by (a) moving the first contact towards the second contact, (b) twisting the first contact relative to the second contact, and (c) pulling on a cord.

Another aspect of the invention includes a catheter valve having a conduit that defines a lumen. The catheter valve includes a spring that is configured to bias the lumen from an open position to a closed position, by decreasing a circumference of at least a portion of the conduit by at least 1 mm.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
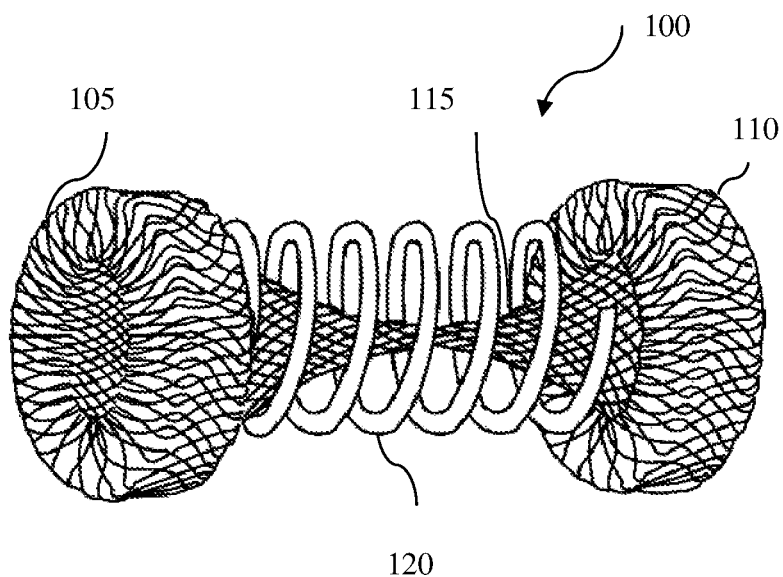
FIG. 1A illustrates a perspective view of one embodiment of catheter constriction valve in a closed configuration.

The inventive subject matter provides a constriction valve, especially for use in cardiac catheterization, urinary catheterization or any other catheterization to the body area with a high fluid pressure. Further, the inventive subject matter includes catheters that include the inventive constriction valves and methods of using such valves and catheters.

While the inventive subject matter is susceptible of various modification and alternative embodiments, certain illustrated embodiments thereof are shown in the drawings and will be described below in detail. It should be understood, however, that there is no intention to limit the invention to the specific form disclosed, but on the contrary, the invention is to cover all modifications, alternative embodiments, and equivalents falling within the scope of the claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

One aspect of the inventive subject matter includes a catheter valve. The catheter valve includes a conduit, which defines a lumen of the catheter, and a spring around the conduit. The spring is configured to bias the lumen from an open position to a closed position by altering an effective length of the conduit. In a preferred embodiment, the change in effective length of the conduit needed to reconfigure the lumen from an open position to a closed position is at least 10 mm, preferably at least 5 mm, and most preferably at least 1 mm.

As used herein, a lumen is an inside space of a structure. In some embodiments, the shape of the lumen depends on the shape of the conduit. For example, the conduit can a tubular shape, a twisted tubular shape, a cuboid shape, or a triangular prism shape, and the shape of the lumen can be shaped to match the conduit. In other embodiments, the shape of the lumen can be independent from the shape of the conduit. For example, where a conduit has tubular shape, the lumen could have a cuboid shape, or vice versa.

As used herein, the term "closed" with respect to a portion of a lumen means that the cross-sectional flow area of the portion is reduced by at least 20% at the then-current pressure, temperature and other conditions, relative to a fully open position at the same conditions.

As used herein, a spring can include any resilient device that can be pressed and pulled. Any suitable types of springs (e.g., mechanical springs, hydraulic springs, pneumatic springs, etc) that can be to exert tension or absorb movement of the conduit are contemplated. For example, contemplated springs includes helical springs (e.g., a coil spring, a compression spring, an extension spring, a torsion spring, etc), leaf springs, wave springs, hydraulic springs operated by fluids (e.g., gas, liquid, etc.), pneumatic springs filled with compressed air or other types of gas.

Thus, depending on the type of spring used, and the shape and of the valve, a spring is configured to bias the lumen from an open position to a closed position by increasing the effective length of the conduit (e.g., by at least 10 mm, 5 mm, 1 mm, etc.), or by decreasing the effective length of the conduit (e.g., by at least 10 mm, 5 mm, 1 mm, etc.). For example, if the spring is a compression spring and the conduit is configured to be closed when it is stretched, the spring is configured to bias the lumen from the open position to the closed position. For another example, if the spring is an extension spring and the conduit is configured to be closed when it is compressed, the spring is configured to bias the lumen from the close position to the open position.

Figure 1B:
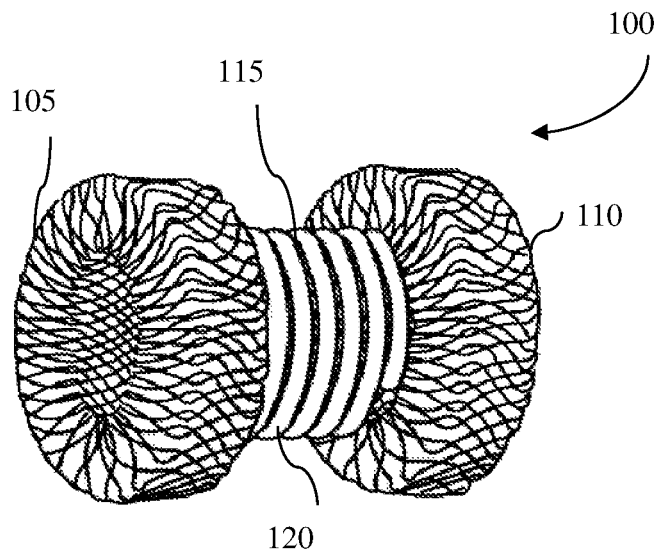
FIG. 1B illustrates a perspective view of the catheter constriction valve of FIG. 1A in an open configuration.

FIGS. 1A-B illustrate one embodiment of the constriction valve 100 for a catheter in an at last partially closed configuration (FIG. 1A) and in an open configuration (FIG. 1B). The constriction valve 100 includes an elongated conduit 115 having a proximal end 105 and a distal end 110. The constriction valve 100 further includes helical coil spring 120 coupled with (e.g., wrapped around) the surface of the conduit 115.

In this embodiment, it is contemplated that any suitable types of materials or structures can be used to increase or decrease the valve's length upon the force or pressure exerted by the spring. Preferably, the conduit 115 comprises a mesh (e.g., extruded, oriented, expanded, woven, tubular, knitted, welded, photochemically etched, electroformed, etc.). The mesh can also be made from any suitable type of material(s). For example, the mesh can be made of any or more of plastic materials (e.g., polypropylene, polyethylene, nylon, PVC or PTFE), metal materials (e.g., aluminum, copper, platinum, metal alloys, etc.), or fiber (e.g., cotton, synthetic fiber, glass fiber, etc.).

It is preferred that at least a portion of the mesh is elastomeric, such that compression or expansion of the elastic portion of the mesh can decrease or increase the length of the conduit. However, it is also contemplated that in some embodiments, the mesh is not elastomeric. In these non-elastomeric embodiments, the mesh comprises a network of wires and/or threads, which are coupled together at contact points about which coupled components can pivot, rotate, turn, swivel, revolve or spin, such that the length of the conduit can increase or decrease by the collective movements of the contact points.

In the embodiment shown in FIGS. 1A-B, it is generally preferred that the spring 120 is a compression helical spring, which shortens its length upon an axial force pressing against ends of the spring. Thus, when no axial force is exerted on the spring, the spring is configured to be in its extended configuration, which increases the length of a constricting portion of the conduit 115. Increase of the conduit length stretches the surface of the conduit, which in turn decreases the diameter of the lumen of the conduit, and biases the conduit from an at least partially open configuration to a more closed configuration. However, in some other embodiments, it is contemplated that the spring 120 is an extension helical spring, which stretches upon action of an axial tensioning force. Thus, when no axial force is exerted on the spring, the spring is configured to be in its compressed configuration, which decreases the length of a constricting portion of the conduit 115. Decrease of the conduit length increases the diameter of the lumen of the conduit, which in turn, biases the conduit from an at least partially closed configuration to a more open configuration.

Further, in the embodiment shown in FIGS. 1A-B, it is contemplated that the spring 120 has a tension or compression strength such that the conduit 115 is in the closed position below an intraluminal pressure of 15 mmHg, preferably below 10 mmHg, and more preferably below 5 mmHg. It is also contemplated that the spring 120 has a tension or compression strength such that the conduit 115 is in the open position above an intraluminal pressure of 15 mmHg, preferably above at least 20 mmHg, and more preferably above at least 25 mmHg. In most cases, insertion of a device (e.g., a needle, a tube, a stent, etc.) into the lumen of the closed conduit will increase the intraluminal pressure above 15 mmHg, and would therefore change the conduit from a closed configuration to an open configuration. Presumably, removal of the device from the lumen of the open conduit would then reduce the intraluminal pressure below 15 mmHg, and would therefore change the conduit from an open configuration to a closed configuration.

FIG. 1A-B should be contemplated to include a valve that is biased only partially closed, providing a relatively narrow opening that allows for relatively slow passage of the passing fluid. For example, a catheter could have a constriction portion with a sufficiently narrow opening such that blood flowing through the opening under a pressure of 50 mmHg can flow, but at a desirably slow rate. The constriction portion can still comprise a mesh having sufficiently flexibility to accommodate an inserted tool of relatively large cross-section.

Figure 2A:
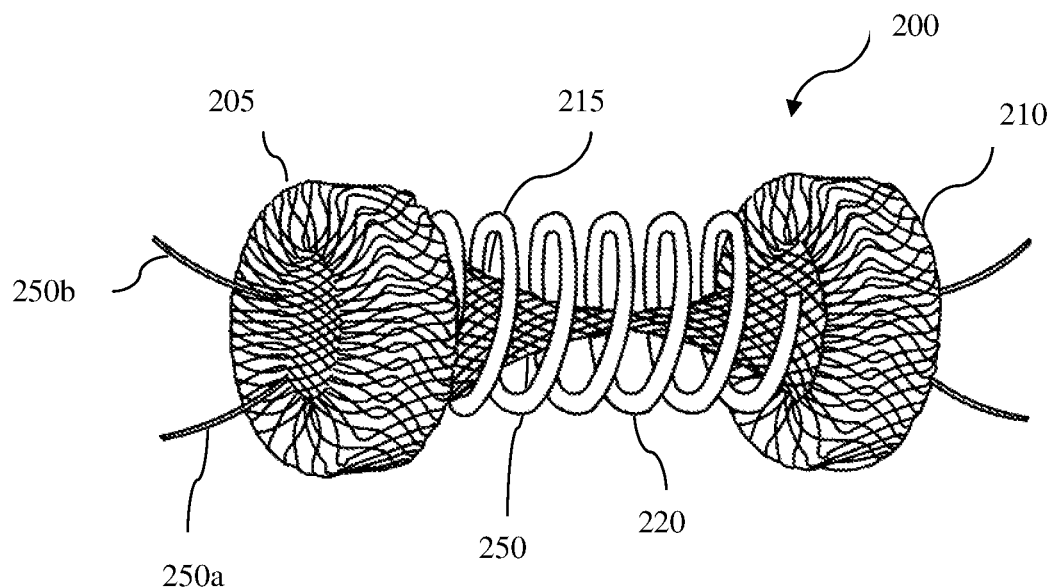
FIG. 2A illustrates a perspective view of another embodiment of catheter constriction valve in a closed configuration.
Figure 2B:
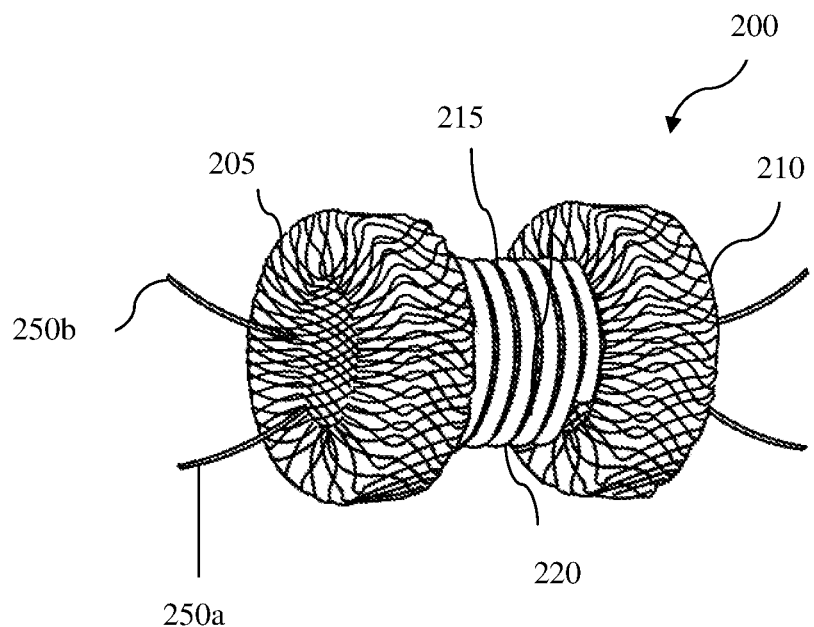
FIG. 2B illustrates a perspective view of the catheter constriction valve of FIG. 2A in an open configuration.

In FIGS. 2A-B constriction valve 200 generally includes an elongated conduit 215 having a proximal finger contact 205, a distal finger contact 210, and helical coil spring 220 coupled with (e.g., wrapped around) the surface of the conduit 215. FIG. 2A shows the constriction valve 200 in an at last partially closed configuration, and FIG. 2B shows the constriction valve 200 in an open configuration.

In this embodiment, the constriction valve 200 further includes a cord 250 that is coupled with the coil spring 220. In this particular embodiment, cord 250 has two ends 250A, 250B, and is tied to the distal finger contact 210 at 252. Pulling on either or both of the two ends 250A, 250B moves the proximal distal and finger contacts 205, 210 towards each other. Cord 250 can be coupled to distal finger contact 210 in any suitable manner, including for example, bonding, welding, and suturing. Pulling on either or both of the two ends 250A, 250B will decrease the length of the conduit 215, and thereby changes the conduit 215 from a closed configuration to an open configuration.

In FIGS. 2A-B, the cord 250 is wrapped around or weaved into the surface of the conduit 215. In other embodiments, the cord 250 can be placed within the lumen of the conduit 215. In still other embodiments, it is contemplated that the cord 250 can be attached to the coil spring 220, having minimal contact with the surface of the conduit 215.

Figure 3A:
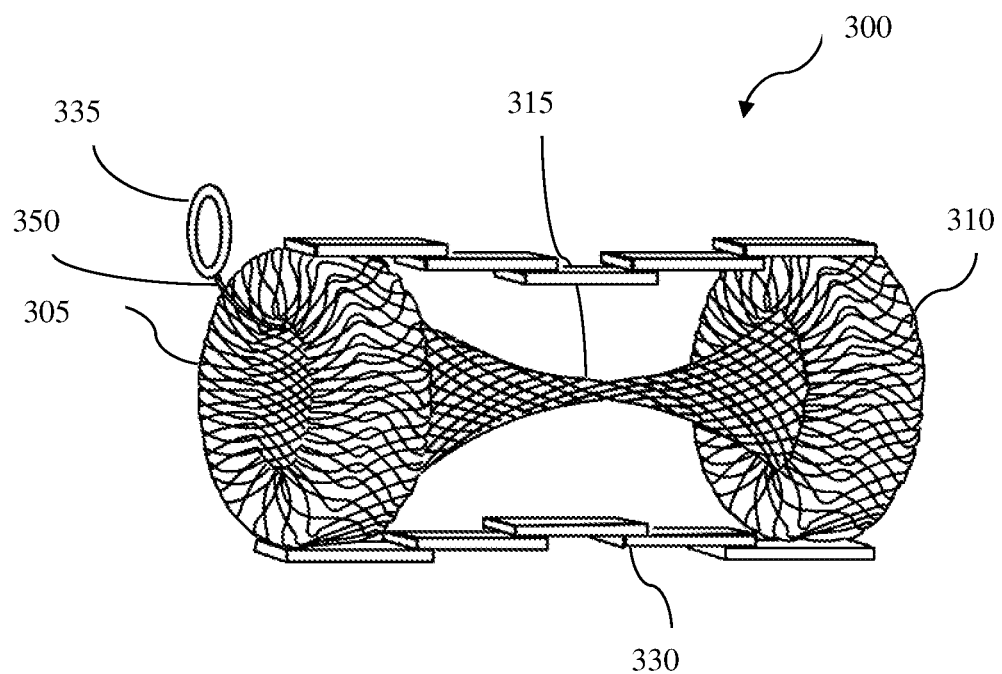
FIG. 3A illustrates a perspective view of another embodiment of catheter constriction valve in a closed configuration.
Figure 3B:
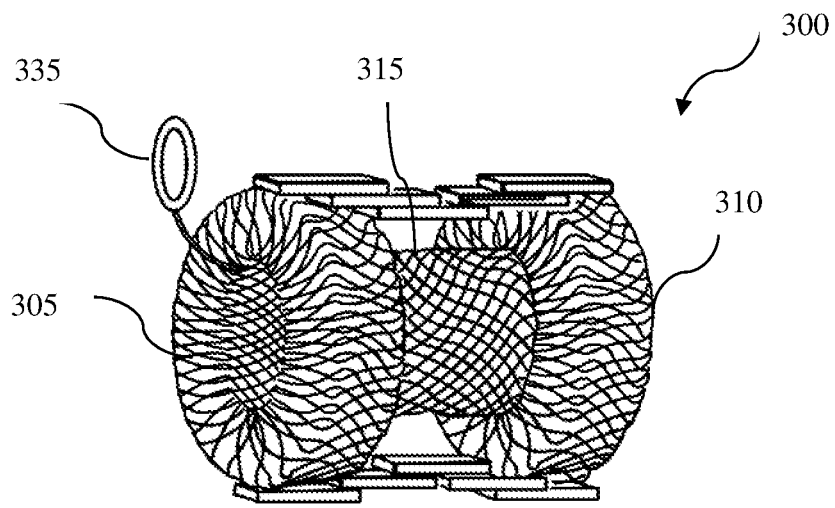
FIG. 3B illustrates a perspective view of the catheter constriction valve of FIG. 3A in an open configuration.

In FIGS. 3A-B an alternative constriction valve 300 again includes an elongated conduit 315 having a proximal finger contact 305 (proximal end) and a distal finger contact 310 (distal end), and does not show, but should be interpreted to include, a helical coil spring coupled with the surface of the conduit 315, and a cord coupled with the surface of the conduit 315. FIG. 3A shows the constriction valve 300 in an at last partially closed configuration, and FIG. 3B shows the constriction valve 300 in an open configuration.

In this embodiment, however, the constriction valve 300 further includes a finger holder 335 that is coupled with the cord 350. The finger holder 335 is depicted as a ring, but should be interpreted generically to include a hook, or in any suitable shape that can be used to facilitate transfer of a pulling force against the cord 350. The finger holder 335 can comprise any suitable type of material or materials. For example, the finger holder 335 can be made of plastic materials (e.g., polypropylene, polyethylene, nylon, PVC or PTFE), metal materials (e.g., aluminum, copper, platinum, metal alloys, etc.), or fiber (e.g., cotton, synthetic fiber, glass fiber, etc.).

Pulling of the finger holder 335 pulls the distal finger contact 310 toward the proximal finger contact 305. Unless the force is evenly distributed along circumference of the conduit 315, the conduit 315 will experience a bending force. To prevent bending of the conduit 315, constriction valve 300 further includes an anti-bending mechanism 330. In FIG. 3 the anti-bending mechanism 330 comprises a telescoping structure having a plurality of telescoping members. At least one telescoping member is attached to each of the proximal finger contact 305 (proximal end) or the distal finger contact 310 (distal end). All other suitable anti-bending mechanisms are contemplated, including for example, two opposite-facing curved elements (not shown). In that embodiment, each curved element could have a proximal end and a distal end, with the proximal end coupled (e.g., affixed, attached, etc) to the proximal finger contact 305 (proximal end), and the distal end is coupled (e.g., affixed, attached, etc) to the distal finger contact 305 (distal end).

Other contemplated catheter valves operate without necessarily incurring a change in length of the conduit. For example, either the conduit, one or more members about the conduit, or some combination of both can be twisted in a manner that alters a circumference of at least a portion of the conduit. In a preferred embodiment, the effective circumference of the conduit changed to bias the lumen from an open position to a closed position is at least 10 mm, preferably 5 mm, and most preferably 1 mm.

In a manner similar to that described above, it is contemplated that constricted portions of twisting embodiments can be closed below an intraluminal pressure of 15 mmHg, preferably below 10 mmHg, and more preferably below 5 mmHg, and opened above an intraluminal pressure of at least 15 mmHg, preferably above at least 20 mmHg, and more preferably above at least 25 mmHg. Increase in intraluminal pressure can, of course, be effected by inserting a device (e.g., a needle, a tube, a stent, etc.) of sufficient cross-sectional area into the lumen of the closed conduit.

Figure 4:
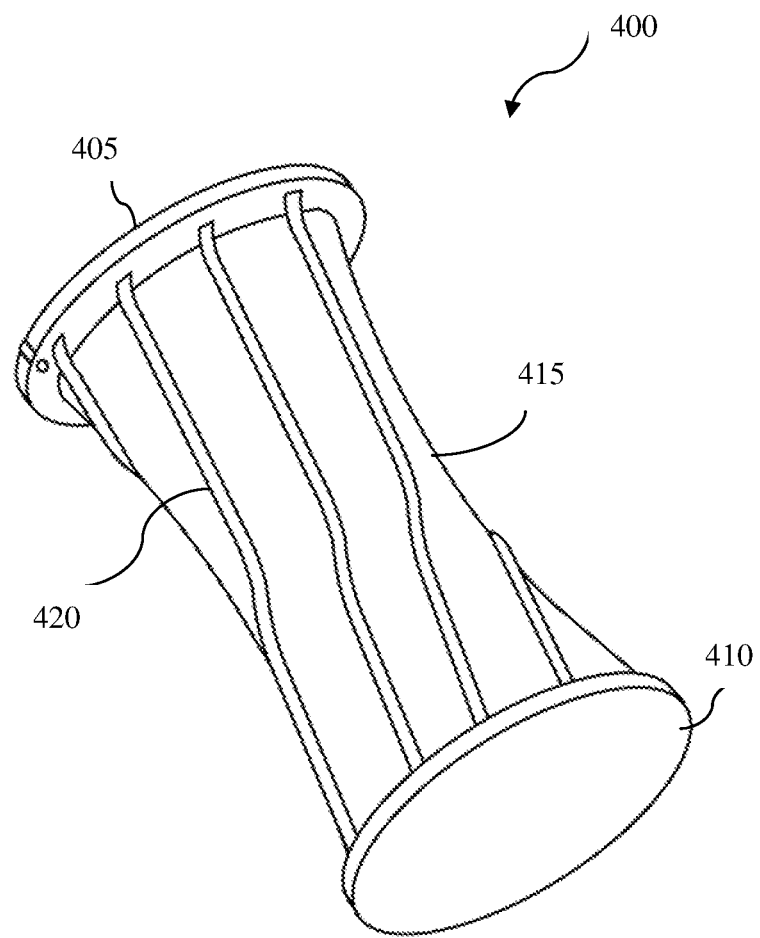
FIG. 4 illustrates a perspective view of another embodiment of catheter constriction valve in an open configuration.

In FIG. 4 a constriction valve 400 includes an elongated conduit 415 having a proximal finger contact 405 and a distal finger contact 410. In this embodiment, the constriction valve 400 further includes a spring 420 having a plurality of fingers that curvatively disposed around the conduit (e.g., helical torsion spring, etc.). As used herein, a finger of the spring 420 refers a single coil or thread that stretches from the proximal finger contact 405 to the distal finger contact 410. The curvature of the fingers from proximal finger contact 405 to distal finger contact 410 is at least 1 degree, preferably at least 10 degrees, and more preferably at least 20 degrees. FIG. 4 illustrates the constriction valve 400 in an open configuration.

Figure 5A:
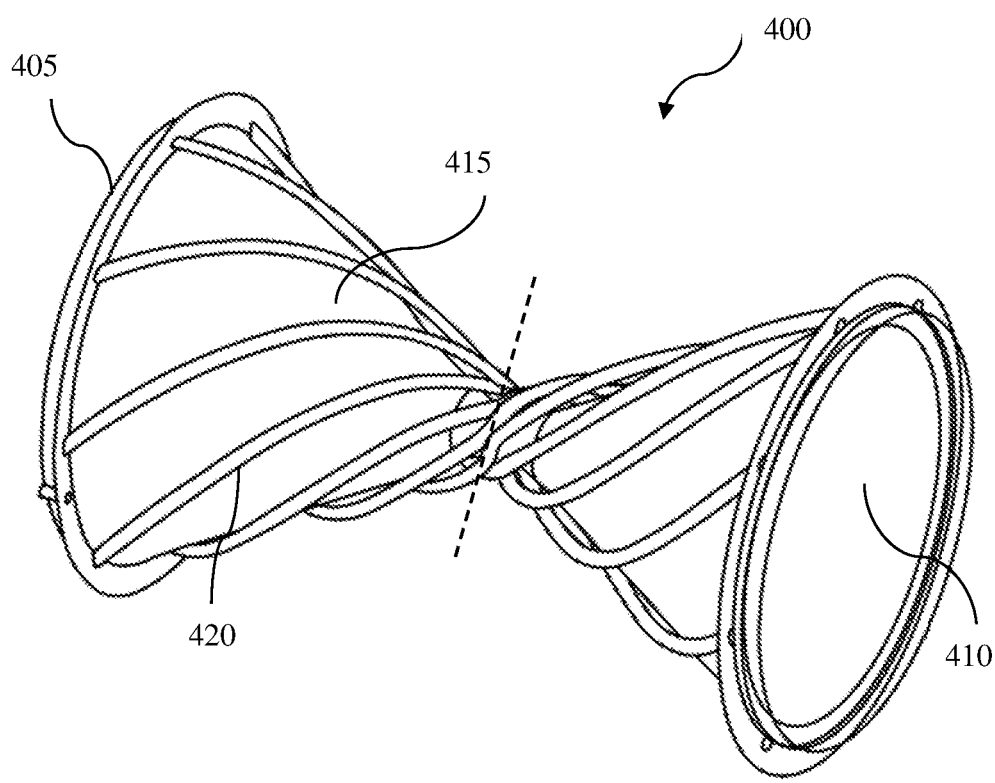
FIG. 5A illustrates a perspective view of the constriction valve of FIG. 4, in a closed configuration.

FIG. 5A illustrates the constriction valve 400 in a closed configuration. In this configuration, it is contemplated that the spring 420 is twisted by relative rotational movements of the proximal finger contact 405 and the distal finger contact 410 (e.g., clockwise for the proximal finger contact and counterclockwise for the distal finger contact). Such twisting exerts pressure onto the surface of the conduit 415, especially more pressure toward the center of the conduit (e.g., middle section between the proximal finger contact 405 and the distal finger contact). Constriction that results from twisting will likely cause a gradual narrower towards the center of the conduit 415, so that the circumference of the lumen at the region of greatest constriction can be less than 20% (and more preferably less than 10%) of the circumference of the lumen at one of the proximal finger or distal finger contacts 405, 410.

In some embodiments, where the conduit 415 comprises a resilient material (e.g., rubber, fibers, etc.), exerting gradual pressure over the surface of the conduit 415 can effectively decrease the circumference of at least a portion of the conduit 415, and thereby change the conduit from the open configuration to the closed configuration. Thus, in turn, releasing the pressure from the surface of the conduit 415 by untwisting the spring 420 can effectively increase the circumference of the conduit 415 back to the original circumference of the conduit, and thereby change the conduit from the closed configuration to the open configuration.

Figure 5B:
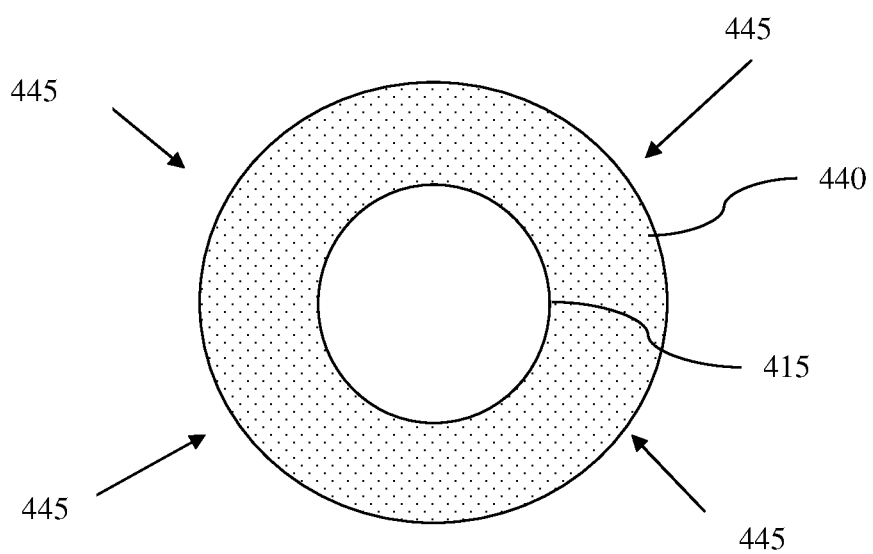
FIG. 5B illustrates a cross-section of a constriction portion the constriction valve of FIG. 5, depicting compression of an optional fluid bag around the conduit.

FIG. 5B shows a cross section of FIG. 5A along the dotted line. In FIG. 5B, an optional fluid bag 440 is disposed around the conduit 415, and pushing inwardly on conduit 415 under force of the spring 420, as depicted by arrows 445. Fluid bag 440 can comprise plastic, rubber, or any other suitably resilient material(s), and can contain a pressurized gas, liquid, gel, or any other suitable fluid.

Figure 6:
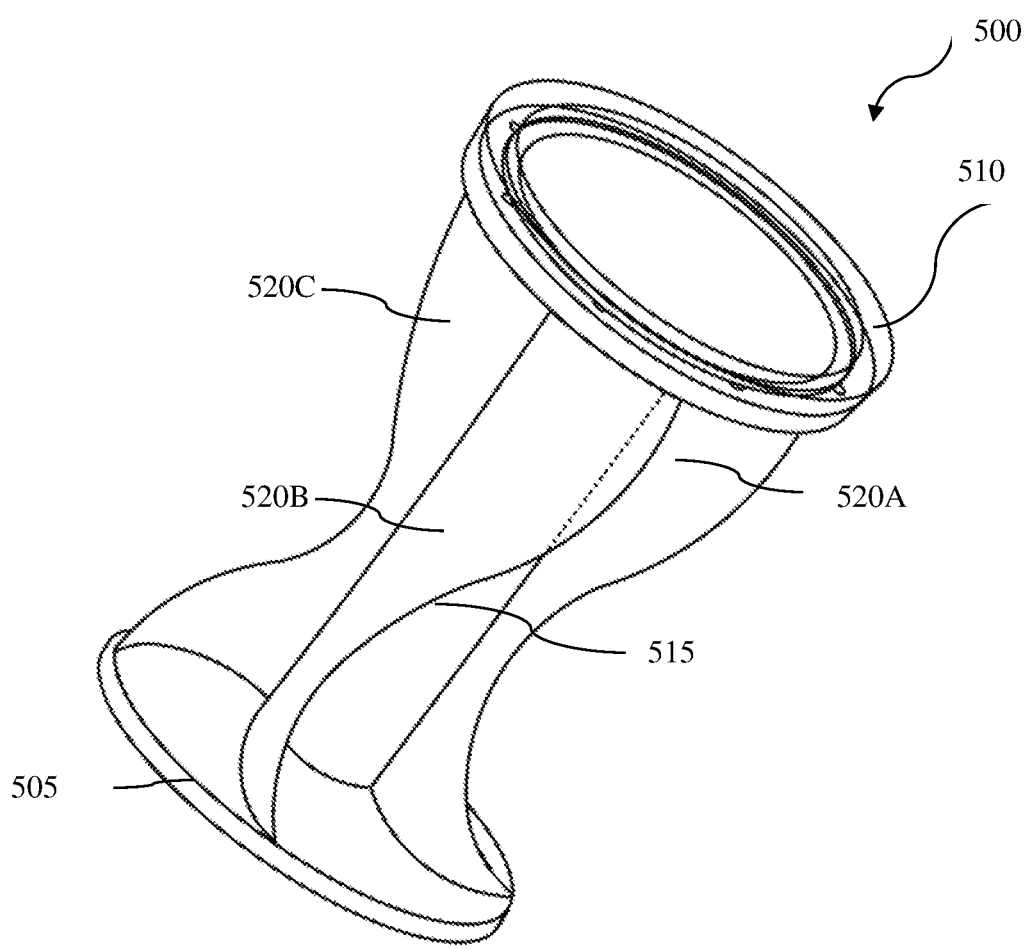
FIG. 6 illustrates a perspective view of another embodiment of catheter constriction valve housed in a catheter.

In FIG. 6 constriction valve 500 again includes an elongated conduit 515 having a proximal finger contact 505 and a distal finger contact 510, but here includes a spring 520 having a plurality of leaves (e.g. 520A, 520B, 520C) that are curvatively disposed around the conduit.

Preferably, each leaf of the spring 520 comprises a curved diaphragm having a proximal end and a distal end. At least a portion of the proximal end of the leaf is attached (e.g., affixed, etc) to at least a portion of the proximal finger contact 505, and at least a portion of the distal end of the leaf is attached (e.g., affixed, etc) to at least a portion of the distal finger contact 510.

In a preferred embodiment, the spring 520 comprises a resilient or elastomeric material such that the spring 520 is twisted by relative rotational movements of the proximal finger contact 505 and the distal finger contact 510 (e.g., clockwise for the proximal finger contact and counterclockwise for the distal finger contact). Such twisting exerts pressure onto the surface of the conduit 515, especially more pressure toward the center of the conduit (e.g., middle section between the proximal finger contact 505 and the distal finger contact). Constriction that results from twisting will likely cause a gradual narrower towards the center of the conduit 515, so that the circumference of the lumen at the region of greatest constriction can be less than 20% (and more preferably less than 10%) of the circumference of the lumen at one of the proximal finger or distal finger contacts 505, 510. The constricting mechanism of FIG. 6 is thus similar to that of FIG. 5, with a major exception that the constricting mechanism of FIG. 6 operates more like a camera shutter.

Another aspect of the invention includes a catheter that includes any of the inventive valves. Contemplated catheters include an elongated body having a proximal end and a distal end, and a valve positioned at the distal end of the elongated body. As used herein, the proximal end refers to an end close to the user (e.g., a medical provider, a technician, etc.) and the distal end refers to an end close to the patient.

The elongated body can be in various shapes (e.g., a tube shape, a cuboid shape, a triangular prism shape, etc.). In a preferred embodiment, the elongated body comprises at least a partially elastomeric material (e.g., a rubber, a plastic, etc.). However, it is also contemplated that the elongated body comprises non-elastomeric materials (e.g., metal, etc).

In some embodiments, the catheter includes a main catheter branch and one or more side catheter branches at its distal end. The side branches can branch out at one or more multifurcation points. Preferably, the constriction valve is located in the main branch of the catheter so that it can constrict the backflow of the fluid from the body upon removal of the devices inserted into the catheter. The distal end of the valve can be positioned at any suitable distance from the first multifurcation point, preferably at least within 5 cm, more preferably within 3 cm, and most preferably within 1 cm.

In FIG. 7 catheter 600 again includes an elongated body 635 and a constriction valve 602 located inside the elongated body 635, an elongated conduit 615 having a proximal finger contact 605 and a distal finger contact 610. In this embodiment, the constriction valve 602 further includes a spring 650 having a plurality of fingers that curvatively disposed around the conduit 615 (e.g., helical torsion spring, etc.).

Figure 7:
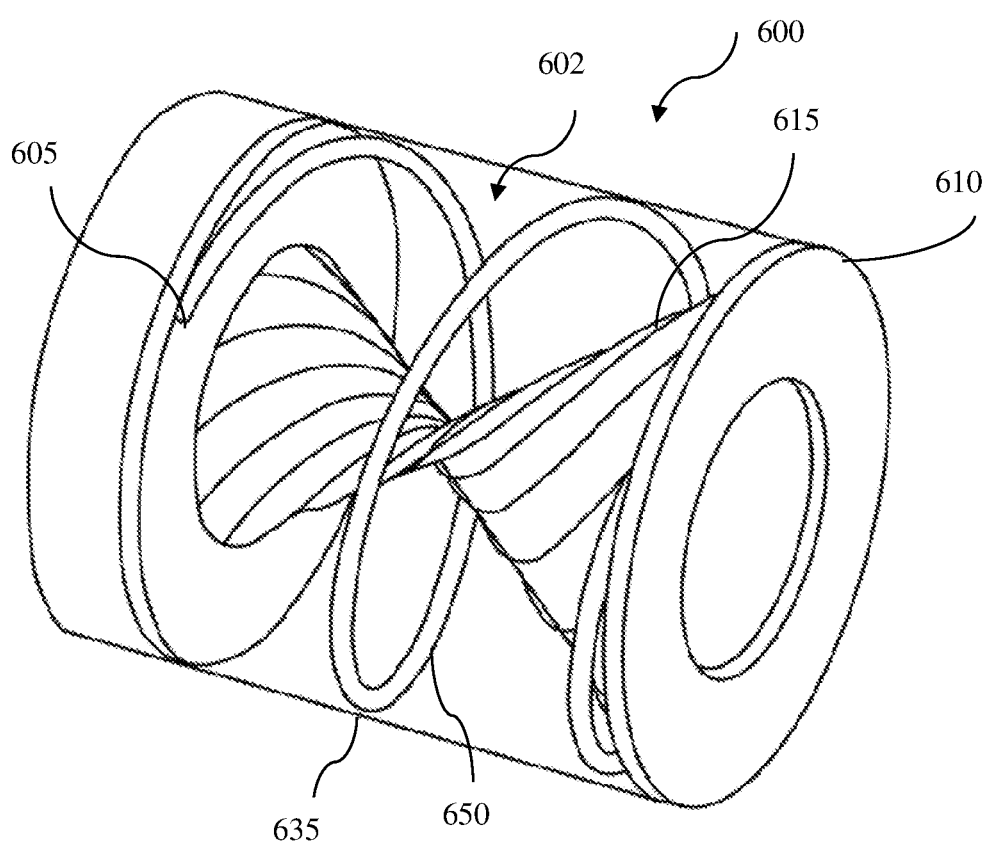
FIG. 7 illustrates a perspective view of another embodiment of catheter constriction valve.

The constricting mechanism of FIG. 7 is similar to that of FIGS. 5 and 6 with a major exception that the constriction valve 602 includes a helical coil spring 650 coupled with (e.g., wrapped around) the surface of the conduit 615. By having two different types of springs, the constriction valve can be closed either by pulling the distal end 610 of the valve 602 closer to the proximal end 605 of the valve 602, or by twisting the distal end 610 of the valve 602 relative to the proximal end 605 of the valve.

Figure 8A:
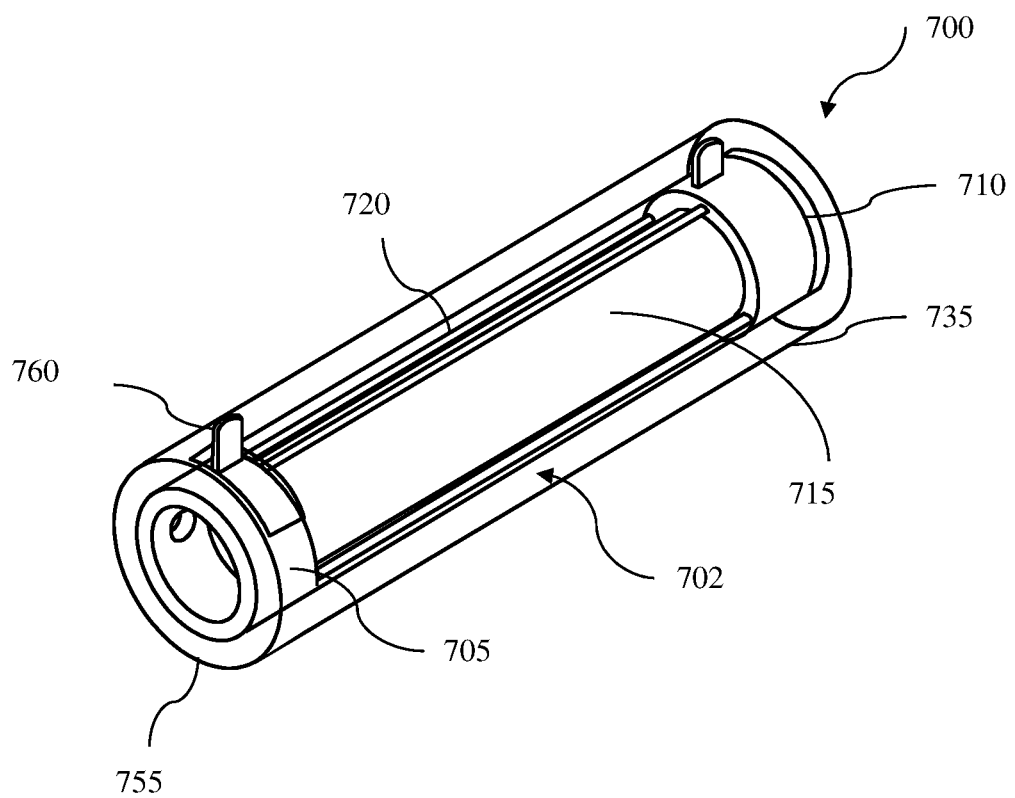
FIG. 8A illustrates a perspective view of another embodiment of catheter constriction valve housed in a catheter in an open configuration.
Figure 8B:
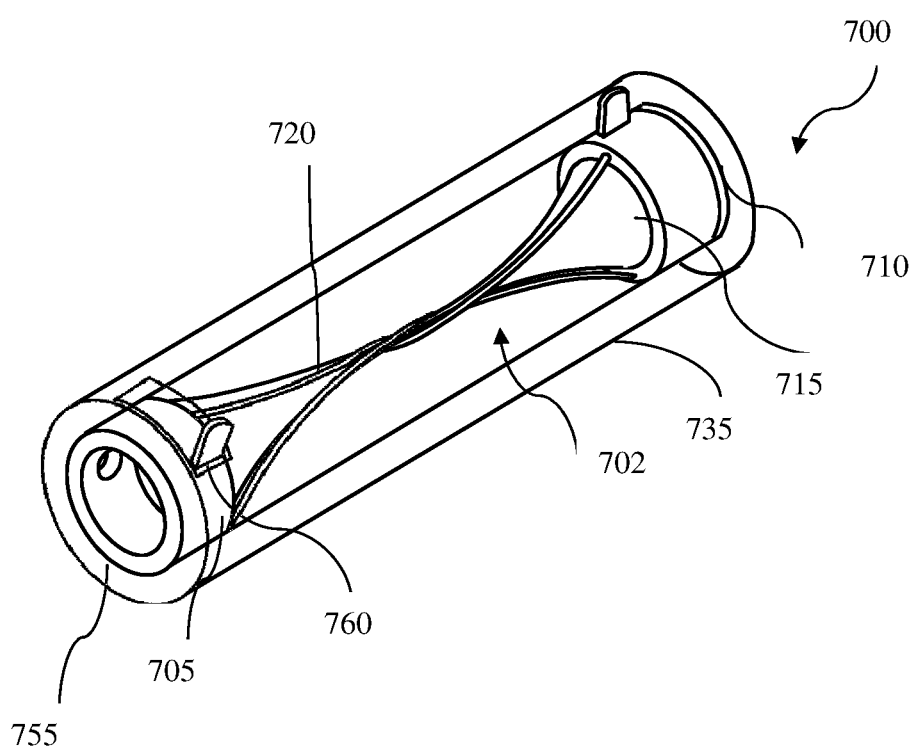
FIG. 8B illustrates a perspective view of the catheter constriction valve of FIG. 8A in a closed configuration.

FIGS. 8A-B illustrate a catheter 700. FIG. 8A shows a catheter 700 with a constriction valve 702 in an open configuration, and FIG. 8B shows the same catheter 700 with constriction valve 702 in an at least partially closed configuration. The catheter 700 includes an elongated body 735 and a constriction valve 702 located inside the elongated body 735. The constriction valve 702 includes an elongated conduit 715 having a proximal finger contact 705 and a distal finger contact 710, and a spring 720 having a plurality of fingers that curvatively disposed around the conduit 715 (e.g., helical torsion spring, etc.).

In this embodiment, the catheter includes a controller 760 coupled with at least a portion of the proximal end 705 via an elongated opening 755 on the elongated body 735 of the catheter 700. The controller 760 is depicted as a stick handle, but should be interpreted generically to include a handle, a button, or in any suitable shape that can be used to facilitate transfer of a rotating force against the proximal end 705. The proximal end 705 of the valve can be rotated as the controller 760 is moved along the elongated opening 755. When the proximal end 705 is rotated relative to the distal end 710 of the valve, the spring 720 coupled to the proximal end 705 and the distal end 710 is twisted such that the twisted springs 720 exerts pressure onto the surface of the conduit 715. Thus, the constricting mechanism of FIG. 8 is similar to that of FIGS. 5, 6, and 7.

Another aspect of the invention includes a method of inserting a tool into a catheter having a constriction valve having proximal and distal finger contacts described one of FIGS. 1-8. In a preferred method, a user inserts a tool into a catheter by manipulating a valve to expand a substantially closed lumen to change the valve from a closed configuration to an open configuration. In one embodiment, the user can manipulate the valve by moving one of the proximal and distal finger contacts towards with each other. In another embodiment, the user can manipulate the valve by twisting or rotating the one of the proximal and distal finger contacts relative to another. Still in another embodiment, the user can manipulate the valve by pulling on a cord, which is coupled to at least one of the proximal and distal finger contacts of the valve.

In a case where the intraluminal pressure generated by inserting a tool is less than a threshold pressure for the spring to be expanded or compressed (or twisted), the valve can be manipulated to change the valve into an open configuration prior to inserting the tool into the lumen of the valve. However, in a case where the intraluminal pressure generated by inserting a tool is more than a threshold pressure for the spring to be expanded or compressed (or twisted), the manipulating step is performed following partial insertion of the tool into a lumen of the valve.

Manipulation of the valve can be performed in various ways. For example, it is contemplated that a user can directly pull, push, twist, or rotate a portion of the valve using the user's finger pressure to operate the valve against the force (e.g., tension) of a spring. However, it is also contemplated that a user can operate an electronic system (e.g., by pushing a button, touching a screen, etc.) that is configured to operate the movement of a spring of the valve.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A catheter valve, comprising:
  a conduit having a proximal end and a distal end, wherein the conduit defines a lumen, and further wherein the conduit comprises a mesh having at least a portion that is elastomeric;
  a biasing member disposed between the proximal end and the distal end of the conduit;
  wherein the biasing member comprises (1) an extended configuration in which the biasing member is configured to stretch the conduit outwardly along an axis to thereby cause the lumen to decrease to a first diameter and partially close the conduit, and (2) a compressed configuration above a first intraluminal pressure in which the biasing member is compressed to thereby allow the conduit to collapse inwardly along the axis and cause the lumen to increase from the first diameter to a second diameter to open the conduit.

2. The valve of claim 1, wherein the biasing member is configured to bias the conduit from an open position to a partially closed position by stretching the conduit and thereby increasing the effective length of the conduit by at least 1 mm.

3. The valve of claim 1, wherein the first intraluminal pressure is 25 mmHg.

4. The valve of claim 1, wherein the biasing member is configured to bias the lumen to a partially closed position solely by stretching the conduit along the axis to thereby cause the lumen to decrease to the first diameter.

5. The valve of claim 1, wherein the biasing member is in the extended configuration below a second intraluminal pressure of 10 mmHg.

6. The valve of claim 1, wherein the biasing member is coupled with a cord wrapped around at least a portion of the conduit, and configured such that pulling on the cord opens the conduit.

7. The valve of claim 1, further comprising a first and second finger contacts, and a cord mechanically coupled to the first finger contact such that pulling on the cord moves the first finger contact towards the second finger contact.

8. The valve of claim 7, further comprising a finger holder coupled to the cord such that pulling on the finger holder moves the first finger contact towards the second finger contact.

9. The valve of claim 1, further comprising an anti-bending mechanism disposed along the conduit.

10. The valve of claim 9, wherein the anti-bending mechanism comprises a plurality of telescoping members.

11. The valve of claim 1, wherein the first diameter is at least 20% smaller than the second diameter.

12. The valve of claim 1, wherein the biasing member is configured to transition between the extended configuration and the compressed configuration due to changes in intraluminal pressure.

13. The valve of claim 12, wherein the biasing member is a spring.

* * * * *